United States Patent [19]

Chang et al.

[11] 4,127,329

[45] Nov. 28, 1978

[54] RAMAN SCATTERING SYSTEM AND METHOD FOR AEROSOL MONITORING

[75] Inventors: Richard K. Chang, Hamden; Richard G. Stafford, New Haven, both of Conn.

[73] Assignee: Northeast Utilities Service Company, Berlin, Conn.

[21] Appl. No.: 752,911

[22] Filed: Dec. 21, 1976

[51] Int. Cl.² .............................................. G01J 3/44
[52] U.S. Cl. ................................................ 356/301
[58] Field of Search .......................... 356/75, 103, 104

[56] References Cited

U.S. PATENT DOCUMENTS

| 3,516,744 | 6/1970 | Hinman et al. | 356/75 |
| 3,704,951 | 12/1972 | Chupp | 356/75 |
| 3,723,007 | 3/1973 | Leonard | 356/75 |
| 3,820,897 | 6/1974 | Roess | 356/75 |

FOREIGN PATENT DOCUMENTS 2,264,292   10/1975   France ...................................... 356/75

OTHER PUBLICATIONS

Rosasco et al., Applied Spectroscopy, vol. 29, No. 5, Sep./Oct. 1975, pp. 396–404.
Stevens et al., *IEEE Transactions on Nuclear Science,* vol. NS-22, No. 2, Apr. 1975, pp. 849–855.
Fouche et al., *Journal of Applied Physics,* vol. 43, No. 9, Sep. 1972, pp. 3846–3851.
Stafford et al., "Laser-Raman Monitoring of Ambient Sulfate Aerosols" (Presented at the National Bureau of Standards Eighth Materials Research Symposium on Methods and Standards for Environmental Measurement at Gaithersburg, Md, Sep. 1976).

*Primary Examiner*—F. L. Evans
*Attorney, Agent, or Firm*—Donald J. Hayes

[57] ABSTRACT

A system and method for monitoring the concentration of micron size pollutants in a gas, such as sulphate aerosols in the ambient air. The gas is drawn through a dichotomous sampler which segregates the larger aerosols from the smaller ones. The smaller sized particles of aerosols are concentrated and then flowed through an inspection chamber having a plurality of optical windows. The sample is illuminated by the light beam from a laser, and a plurality of mirrors provide a light trap to redirect the laser radiation to the sample a large number of times. The Raman scattered radiation from the particles is collected by a mirror and by a lens onto a spectrograph which provides spectrally dispersed radiation according to the molecular constituents of the sample. This radiation is detected and converted to electrical signals providing qualitative and quantitative information as to the pollutant composition and concentration.

21 Claims, 5 Drawing Figures

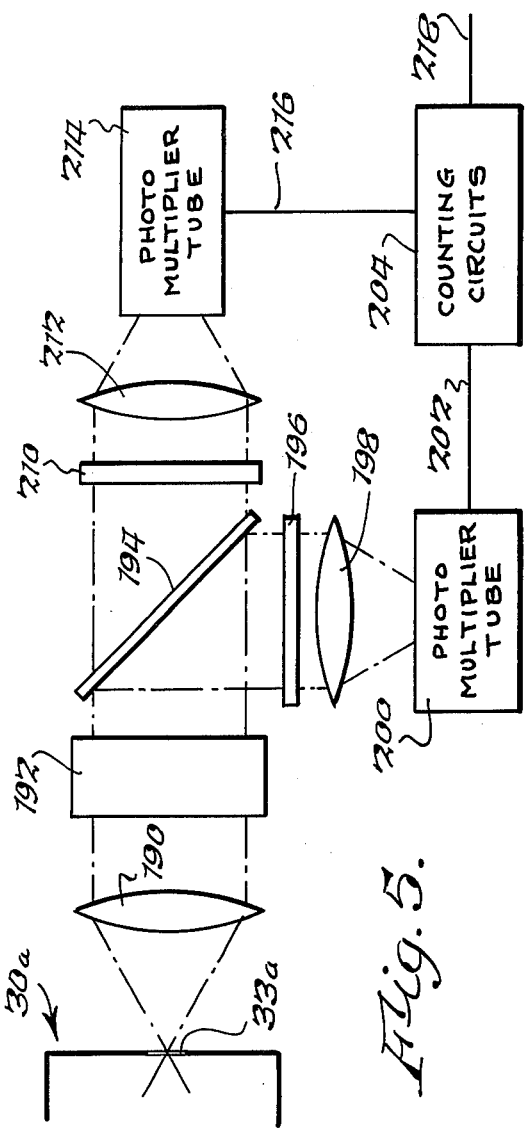
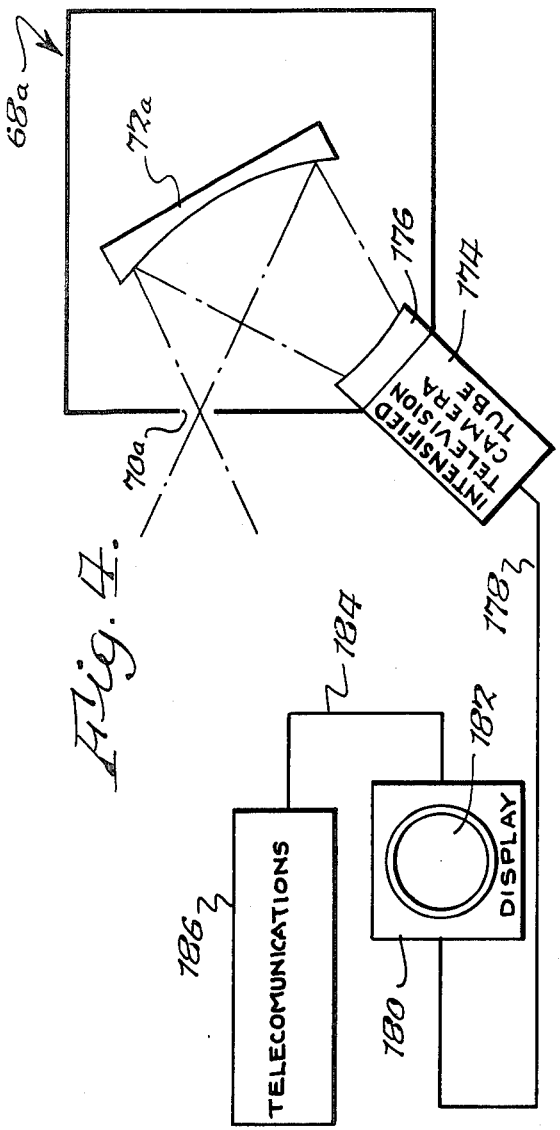
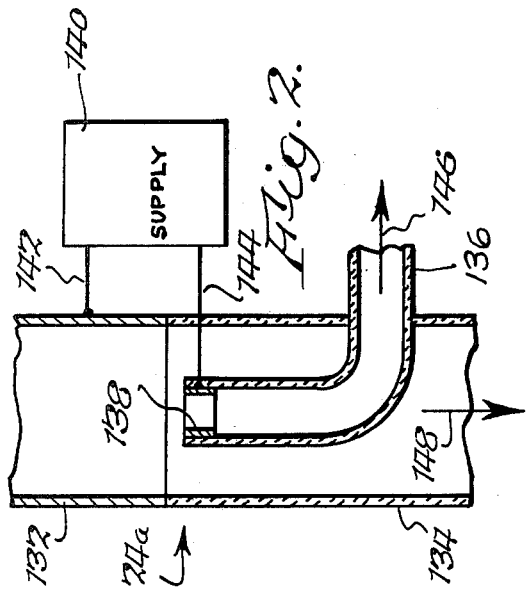
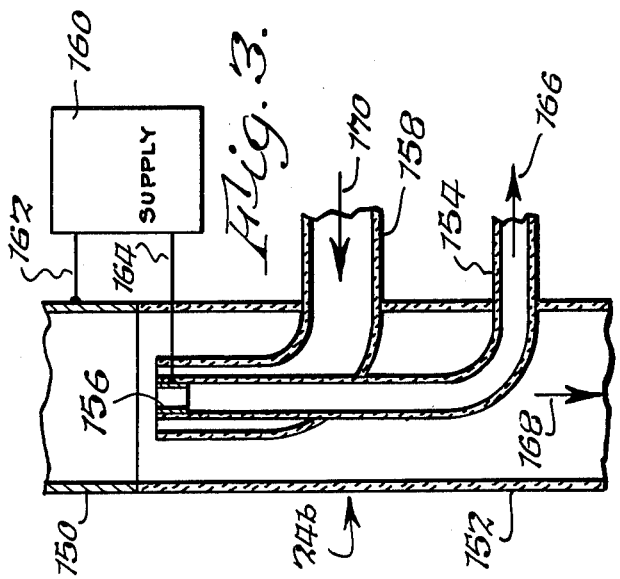

RAMAN SCATTERING SYSTEM AND METHOD FOR AEROSOL MONITORING

BACKGROUND OF THE INVENTION

This invention relates to monitoring of pollutants in a gas, and more particularly to a new and improved system and method for specifying the pollutants and monitoring the concentrations thereof in both the gaseous and aerosol phases.

One area of use of the present invention is monitoring sulphate aerosols in the ambient atmosphere, although the principles of the invention can be variously applied. An aerosol is an aggregate of solid or liquid matter dispersed in the air, and specific aerosols such as sulphates of a size range from about 0.1 micron to about 2.0 microns are considered to be harmful to health. In particular, such particles are not filtered out by the human body whereas larger sizes are filtered out and smaller sizes are believed not to be harmful.

Several problems are associated with methods employed for measurement of aerosol pollutants which involve first, a collection phase where the airborne particles are collected on filters and second, an analytical phase where measurements of the collected particles are made. During the first phase, interparticle reactions may occur on the filter collecting surfaces especially since the particle concentrations are enhanced considerably by collection. With sulphate aerosols, $H_2SO_4$ and $(NH_4)_2SO_4$ are believed to be the major sulfur constituents, and increasing the concentrations of the chemically reactive $H_2SO_4$ and $(NH_4)_2SO_4$ from dilute atmospheric to a concentrated surface deposit on a filter leads to chemical interactions. In addition, $SO_2$ can be converted to $HSO_4^-$ and $SO_4^=$ by catalytic interaction with other particles collected on the filter. Briefly, the aerosols may interact chemically with each other, the filter media, and the ambient gases, e.g., $SO_2$ and $NH_3$, passing through the filter. Therefore, the data resulting from the second phase are not necessarily indicative of the original aerosol concentration. Furthermore, the second phase usually takes place in a laboratory rather than at the monitoring site so that real-time analysis of pollutant concentration is not possible.

SUMMARY OF THE INVENTION

The principal object of this invention is to provide a new and improved system and method for monitoring both ambient gaseous and aerosol pollutants.

It is a further object of this invention to provide such a system and method for monitoring the pollutant concentration directly, in situ, without intervention such as filter collection.

It is a further object of this invention to provide such a system and method for real time monitoring of the pollutant concentration.

It is a further object of this invention to provide a new and improved system and method for measuring the concentration of respirable sulphate aerosols, i.e., those of less than about 2 micron particle size, in the ambient atmosphere.

The present invention provides a system and method for monitoring the concentration of micron-size pollutants in a gas, such as sulphate aerosols in the ambient air, wherein the gas is moved through a dichotomous sampler for particle size separation and the gas flow containing the smaller particles is illuminated by the light beam from a fixed frequency laser. Laser Raman backscattering from the pollutant molecules, aerosols and other atmospheric molecular constituents is optically collected and filtered to provide spectrally dispersed radiation according to the molecular constituents, which radiation is converted to qualitative and quantitative information including pollutant identification and concentration, which information can be in the form of electrical signals. The aerosols can be increased in density by a concentration prior to illumination, and the efficiency of the laser Raman technique is enhanced by an optical trap causing the laser radiation to be redirected a number of times through the sample. A ruby laser has a wavelength which minimizes the excitation of $NO_2$ fluorescence, and operating the laser in a pulsed mode minimizes dark noise in the signal detection. A cavity-dumped (Q-switched) argon ion laser also can be used provided that some post-signal data treatment is applied to reduce the $NO_2$ fluorescence background.

The foregoing and additional advantages and characterizing features of the present invention will become apparent upon a reading of the ensuing detailed description together with the included drawing wherein:

BRIEF DESCRIPTION OF THE DRAWING FIGURES

FIG. 2 is a schematic diagram of one form of the concentrator in the system of FIG. 1;

FIG. 3 is a schematic diagram of another form of the concentrator in the system of FIG. 1;

FIG. 4 is a schematic block diagram of an alternative detector for the system of FIG. 1; and FIG. 5 is a schematic block diagram of a filter combination for use as an alternative in the system of FIG. 1.

DETAILED DESCRIPTION OF THE ILLUSTRATED EMBODIMENTS

Figure 1:
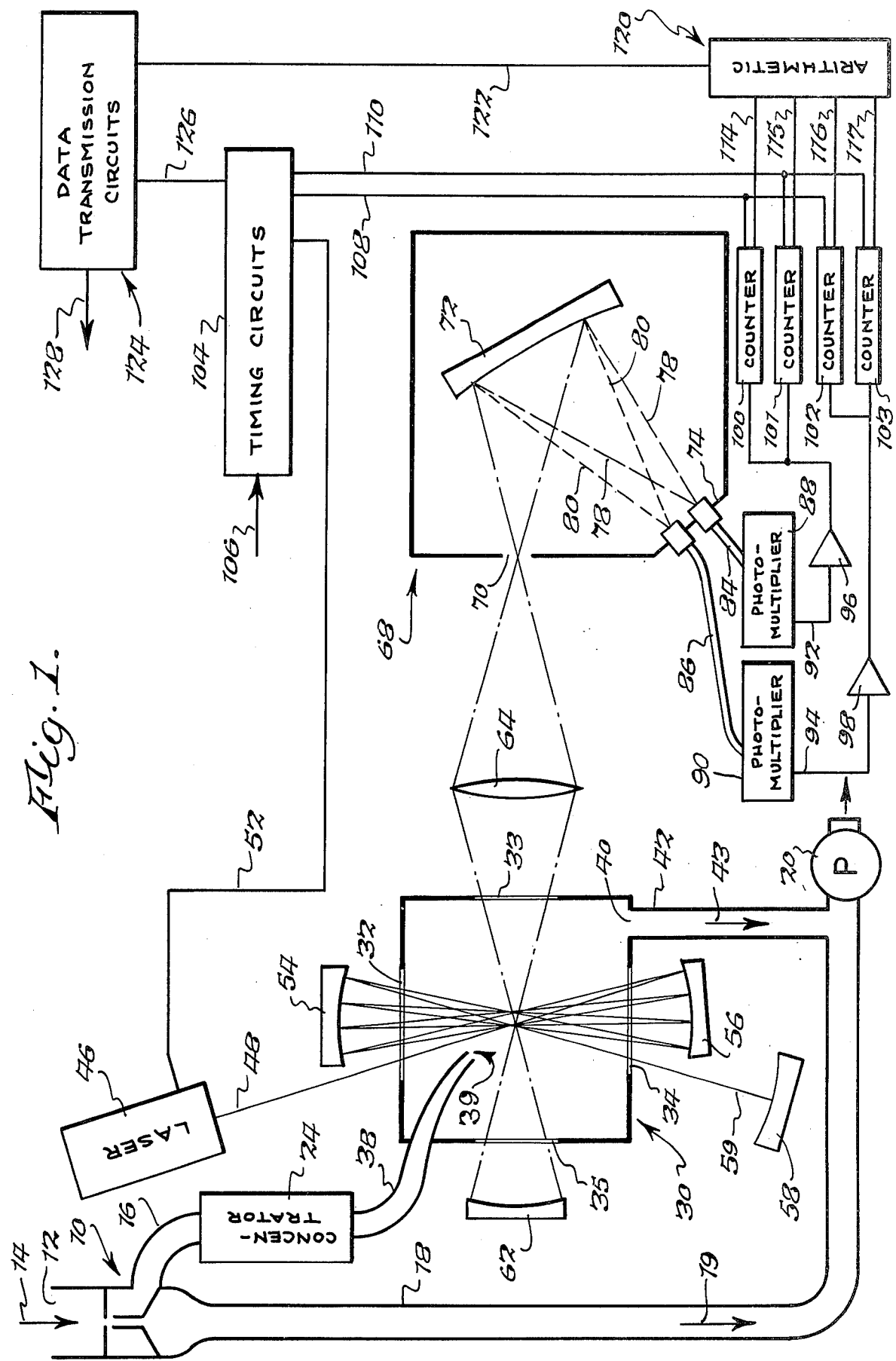
FIG. 1 is a schematic block diagram of a system according to the present invention for monitoring ambient gaseous and aerosol pollutants.

In a basic molecular process leading to Raman scattering, when a collimated laser beam is incident on a sample volume containing a number of molecules, the incident laser photon with energy $h\nu_1$ excites a molecule from its ground state to a virtual intermediate state. A Raman photon of energy $h\nu_2$ then is emitted, leaving the molecule in an excited vibrational state of energy $h\nu_1-h\nu_2$. In general, the scattered Raman photon has a different energy from the incident photon and has no phase correlation with the incident photon. Each chemical species has a unique Raman scattering profile that allows its identification, barring spectral overlap from interfering compounds.

In accordance with this invention, ambient air is flowed through a dichotomous sampler for particle size separation, such as separating aerosols from larger particles, whereupon the sample of interest preferably is concentrated and then flowed through an inspecting chamber having a plurality of optical windows. The sample is illuminated by the light beam from a fixed frequency laser, for example a pulsed ruby or argon ion laser, and an optical trap in the form of a plurality of mirrors causes the laser radiation to be redirected back onto the sample a number of times. The Raman scattered radiation from the aerosols and gases is gathered by a collection mirror and lens onto a spectrograph which optically disperses radiation according to the molecular constituents of the sample. This radiation is detected and converted to electrical signals providing qualitative and quantitative information as to the pollutant compositions and concentrations thereof. A filter combination can be employed in place of the spectrograph where only one pollutant is to be detected.

The system of this invention advantageously provides monitoring of ambient gaseous and aerosol pollutants in situ and in real time. In the laser-Raman technique which is employed, a single laser wavelength can excite all molecules in the gaseous and aerosol phases to scatter at the characteristic Raman radiation of each chemical specie, thereby advantageously avoiding the need to employ different laser wavelengths for different types of molecules. The non-interventive nature of the monitoring avoids any adverse chemical interaction involving the pollutants on a collection substrate, and concentration determinations can be made periodically over extended periods of unattended operation. The data output in the form of electrical signals advantageously can be transmitted to remote locations for use and storage.

In FIG. 1 there is shown a sampling means generally designated 10 having an inlet 12 into which gas to be monitored flows in the direction of arrow 14 and a pair of outlet conduits 16 and 18. Sampling means 10 separates the incoming gas flow into two samples flowing out conduits 16, 18 according to the size of dispersed particles, and in the system shown sampling means 10 comprises a dichotomous sampler which separates aerosol particles of less than 2 microns in size into a sample which flows in conduit 16 and directs the larger aerosols with diameters greater than 2 microns to conduit 18 whereupon this flow is in the direction of arrow 19. Dichotomous sampler 10 can be of various commercially available types, such as those sold by Sierra Instruments and Thermo-Systems, Inc. Conduit 18 is connected to a suction pump 20 which continuously moves or draws ambient air through the gas-handling portion of the system.

The portion of the gas to be monitored flows along conduit 16, and in the system shown conduit 16 is connected to the inlet of a concentrator 24 which functions to concentrate the small aerosol particles flowing along conduit 16 into a relatively narrower stream, while at the same time not causing precipitation of the aerosols. Concentration is employed to enhance detection sensitivity, and aerosol concentration by a factor of approximately 10 to 100 provided by concentrator 24 is believed to be more economical and reliable than employing measures in other portions of the system to increase sensitivity by the same amount. In addition, the air carrying aerosol particles also contains $NO_2$ and other gases which can give rise to interfering effects sufficiently strong to impair sulphate detection sensitivity. Concentrating the aerosol particles into a tighter stream without pressurizing the entire air sample selectively enhances sulfate detection sensitivity. Concentrator 24 will be described in more detail further on in the specification.

A sampling chamber or cell 30 is hollow, rectangular in shape, preferably cubic, and has four optical windows 32, 33, 34 and 35, there being one optical window on each of the four sidewalls which intersect a common plane. Chamber 30 is of suitable gas impervious material which preferably also is opaque. The optical windows are non-fluorescing and are disposed at ninety degree intervals around chamber 30. The interior of chamber 30 receives gas flowing in conduit 16 from sampler 10, and in the system shown the output of concentrator 24 is conveyed by a conduit 38 to the interior of chamber 30. The outlet end 39 of conduit 38 serves as a nozzle to direct the gas flow through the central region of chamber 30. An exit port 40 in one wall of chamber 30 is connected by a conduit 42 to pump 20 which draws gas in the directions indicated by arrows 19, 43 to maintain a flowing system. Sampler 10, concentrator 24, chamber 30, pump 20, and conduits 16, 18, 38 and 42 comprise the gas handling or processing portion of the system.

A laser 46 provides output radiation which is monochromatic and coherent and nearly all propagated in a single direction as indicated by the light beam 48. Laser 46 is positioned with respect to chamber 30 so that the laser beam 48 enters the chamber through one of the optical windows such as window 32 and so that the laser focal volume is located at the center of chamber 30. In order to minimize, if not eliminate, interference from fluorescence caused by $NO_2$ in the ambient air, the laser wavelength should approach the wavelength of infrared radiation. A ruby laser having a red wavelength of 6943Å is desirable. In addition, a pulsed laser is desirable because the pulsed excitation allows gating of electrical components of the system detector and readout circuitry and minimizes dark noise in those portions of the system. Thus, laser 46 can be of the pulsed ruby, non-Q-switched type and typically has the following characteristics: energy of 5 Joules per pulse, pulse duration of $10^{-3}$ seconds, time between pulses of 5 seconds and beam area of about 1 cm$^2$. Alternatively, laser 46 can be a cavity dumped argon ion laser with the following characteristics: average energy of 3 Joules, pulse duration of $10^{-8}$–$10^{-7}$ sec., pusle repitition of 1–10 MHz, and beam area of about 2–3 mm$^2$. The 1/100 second duty cycle minimizes dark current, and post-data treatment is employed to reduce the $NO_2$ fluorescence background. A line 52 connected to laser 46 supplies control signals which synchronize the operation of laser 46 with other components of the system to eliminate noise.

Beam 48 from laser 46 is directed through window 32 into the center of sample cell 30 and interacts with the flow of concentrated aerosols. Only a minute fraction of the laser radiation is dissipated by the Raman scattering process, and a large portion of the radiation is redirected back into the aerosol path by optical means in the form of a plurality of concave mirrors 54, 56 and 58 operatively associated with chamber 30 and which define a light trap. In the system shown, the mirrors 54 and 56 are located outwardly of chamber 30 and adjacent the optical windows 32 and 34, respectively. Mirror 54 is positioned with respect to window 32 in a manner allowing the incoming laser beam 48 to pass uninterrupted through window 32 to the central region of chamber 30. The beam continues along a straight path through the oppositely-located window 34, and mirror 56 is positioned with respect to window 34 to reflect the beam back toward the central region of chamber 30. The laser beam or radiation is partially trapped by the optical cavity defined by the concave mirrors and is caused to traverse or pass through the central region of chamber 30 a large number of times in opposite directions, as shown in FIG. 1. Windows 32, 33, 34, and 35 are all coated with anti-reflection material to minimize reflection. As an alternative arrangement, mirrors 54, 56 and 58 are placed inside chamber 30 in order to minimize reflection loss, which is less than 0.05%, from the two windows 32 and 34.

The two spherical mirrors 54, 56 have equal radii of curvature and are positioned so that the radii are coincident. The incident laser beam 48 passes near the coincident radii of curvature and traverses the central region of chamber 30 and then passes through window 34 in the form of a beam which is reflected back to chamber 30 by mirror 56 and through windows 34 and 32 onto mirror 54. The last exit beam 59 from the light trap consisting of mirror 54 and 56 is redirected back into the light trap by mirror 58. Mirrors 54, 56 and 58 can be of the dielectric coated type having reflectivity of 99.96 percent at 0.6943 or 0.5145 micron wavelength depending on whether a ruby or an argon ion laser is used. The focal region within chamber 30 contains two images each of which intersects the many passes of the laser beam. The foregoing arrangement providing multiple passes of the laser beam enhances the effectiveness of the laser illumination and is believed to increase system efficiency by a factor of approximately 50 as compared to a system employing a single pass of the laser beam through the flow of gas to be monitored.

In the system shown, laser radiation enters and exits through optical windows 32 and 34, respectively, of the sample chamber 30 which windows also can be designated the 0° and 180° windows, respectively. The Raman scattered radiation from the aerosols, pollutant molecules and other molecular constituents of the gas flowing through chamber 30 will exit from the optical windows 33 and 35 which also can be designated the 90° and 270° windows, respectively. In other words, the multiple passes of the laser radiation are in a path between windows 32, 34 and the Raman backscattering is optically collected in a direction substantially perpendicular to the direction of the laser beam. A collection mirror 62 is located outwardly of and in registry with optical window 35 of the chamber 30. Mirror 62 is concave and of sufficient size, i.e. f number, to receive and reflect the Raman backscattering from window 35, and mirror 62 can be in the form of an f/1 aluminized front surface concave mirror. A collection lens 64, for example an f/1 camera lens, is located outwardly of optical window 33 and in registry with mirror 62.

The radiation collected and gathered by the combination of mirror 62 and lens 64 is separated or filtered into various frequency components by a spectrograph generally designated 68 having an entrance slit 70. Spectrograph 64 also serves to filter out the laser radiation frequency. The radiation is focused or imaged onto entrance slit 70 by lens 64. Spectrograph 68 can include a holographic concave optical grating 72 which disperses or separates the radiation into spectral components or images onto an output image or exit surface 74. In particular, grating can be of the type commercially available from Jobin-Yvon Optical Systems having 3600 grooves per millimeter in sizes up to 110 × 110 cm$^2$. Entrance slit 70 and the output image surface 74 are located at the focal points of the concave grating. In the system shown, two spectral images of interest are formed, the lines 78 indicating the separated sulphate radiation frequency component which forms a spectral line image on or adjacent surface 74 and the lines 80 indicating the separated nitrogen radiation frequency component which forms another spectral line image spaced from the sulphate image. The frequency corresponding to the incident laser beam 48 is directed by the grating 72 to some other location within the spectrograph 68 such as an inner wall surface away from the region of the output image surface 74.

The spectral line images thus formed at the output of spectrograph 68 provide qualitative information as to the chemical composition of the particles in the gas flow through chamber 30. The system shown also provides quantitative information in the form of the concentration of such pollutants, i.e., $SO_2$ and micron to submicron size particles such as sulphate aerosols, in the gas flowing through chamber 30. The Raman signals of interest are detected by fiber optic bundles or pipes 84, 86 each having one end positioned at the appropriate location on the spectrograph output image surface 74, i.e. at the appropriate Raman wavelength. In the system shown, light pipe 84 receives radiation at the sulphate image line of interest and light pipe 86 receives radiation at the nitrogen image line for calibration purposes. Light pipes 84, 86 each can have a slit-shaped cross section at the end located at the spectrograph image or exit surface 74 and a round cross section at the opposite end. The output image surface 74 need not be planar, and the fiber optics pipes 84, 86 advantageously minimize or compensate for any aberrations caused by the spectrograph. The light pipes 84 and 86, in turn, are connected to the inputs of photomultipliers 88 and 90, respectively, for converting the radiation signals into electrical signals. Each photomultiplier can be an RCA C31034 photomultiplier tube cooled to about −20° C. by a thermoelectric cooler for photon counting. The resulting dark count is about 1 to 5 per second.

The outputs of photomultipliers 88 and 90 are individual photoelection pulses which are transmitted by lines 92 and 94, respectively, to amplifiers 96 and 98. The output of amplifier 96 is connected to each input of digital counters 100, 101, and the output of amplifier 98 is connected to each input of digital counters 102, 103. The operation of counters 100-103 is controlled by timing circuits generally designated 104 which, in turn can receive command or control signals from an input line 106. A line 108 transmits timing or control signals to counters 100 and 102, and a line 110 transmits timing or control to counters 101, 103. Line 52 connecting timing circuits 104 to laser 46 synchronizes pulsing of the laser with operation of the counter. In particular, during each pulse of laser 46, counters 100 and 102 are operated to count and accumulate the number of sulphate and nitrogen photoelectron pulses, respectively, and counters 101 and 103 are not operated. Between laser pulses, counters 101 and 103 are operated to count and accumulate the number of dark current background pulses and counters 100 and 102 are not operated. The use of four individual counters allows constant monitoring of proper operation of the system. For example, counter 102 serves to indicate the optical integrity of the system in that a decrease in number of nitrogen pulses below a certain level would indicate, for example, misalignment of the spectrograph or stoppage of the aerosol concentrator.

At the end of a typical data accumulation period, the counts accumulated in the counters are transferred to an arithmetic unit 120. In particular, digital signals from counters 100, 101, 102 and 103 are transmitted by lines 114, 115, 116 and 117, respectively, to appropriate inputs of unit 120 which performs the following operations. The total of background current pulses accumulated in counter 101 is subtracted from the total of sulphate photoelectron pulses accumulated in counter 100 to provide a net sulphate count. The total of background current pulses accumulated in counter 103 is subtracted from the total of nitrogen photoelectron pulses accumulated in counter 102 to provide a net nitrogen count. The net sulphate count is divided by the net nitrogen count, and the result is multiplied by a proportionality constant determined from laboratory measurements to provide the sulphate concentration in parts per billion or in micrograms per cubic meter. A digital signal representation of this quantity is transmitted from arithmetic unit 120 by line 122 to data transmission circuits 124 for transmission over a line 128 to a remote data collection and control center. The operation of circuits 124 is controlled by circuits 104 through the connection indicated by line 126.

The operation of the system of FIG. 1 is as follows. Pump 20 is operated to move gas or ambient air through the gas handling portion of the system at a flow rate providing proper operation of the sampler 10. Concentrator 24 provides several advantages as set forth above, but in some applications can be omitted in which case the output of sampler 10 is in direct communication with the inspecting chamber 30. In such a case, rather than being defined by a separate enclosure or vessel, chamber 30 can be defined in sampler 10 within a portion of the sampler housing. One illustrative application of the system and method of the present invention is monitoring smokestack emissions from fossil fuel power plants of an electric utility. In this application and most others, an assembly of sampler 10, chamber 30, pump 20 and the associated conduits, mirrors 54, 56, 58 and 62, lens 64 and concentrator 24 if included can be placed permanently at each location where ambient air or gas is to be monitored. Laser 46 and the detecting components of the system such as spectrograph 68 and the associated photomultipliers and readout apparatus then are brought to each monitoring station, for example on a small truck, only at times when motitoring and measuring are to take place.

Providing laser 46 of the pulsed ruby or cavity-dumped argon ion type gives several advantages as set forth above. Other types of lasers, for example a continuous argon ion laser, can be employed in situations where characteristics of such other lasers are advantageous. For monitoring sulphate aerosols, spectrograph 68 should be operated with an entrance slit width which will enable spectral resolution of the 981 cm$^{-1}$ Raman spectral line for $SO_4^=$ and the 895 cm$^{-1}$ and 1050 cm$^{-1}$ Raman spectral lines for $HSO_4^-$. During a monitoring period pump 20, laser 46 and spectrograph 68 are operated continuously, and a typical monitoring period might be approximately 20 minutes in duration. During this time, laser beam 48 illuminates the gas or aerosols flowing continuously through chamber 30, the laser radiation passing back and forth through the flow many times due to the light trapping action of mirrors 54, 56. The Raman radiation scattered by the gas or particles is collected by mirror 62 and the lens 64 onto the entrance slit of spectrograph 68, and the spectrograph redirects the laser frequency component to somewhere else in spectrometer 68 and separates the Raman radiation by wavelength to provide spectrally resolved images of the chemical species as described in detail above. The photons creating these images are detected and counted by the arrangement of photomultipliers and digital counters. While the arrangement illustrated in FIG. 1 monitors sulphate and nitrogen components of the ambient air, additional photomultipliers and counters can be included for monitoring additional chemical species. While the system shown includes arithmetic unit 120 for calculating the sulphate concentration, data can of course be read from counters 100-103 and the calculations made by operating personnel.

The arrangement of mirrors 54, 56 and 58 can be used with both continuous and pulsed lasers. In a pulsed mode, due to the speed of light, aerosol concentration is still sampled during each of the laser pulses averaged over all the laser pulse firings. The aerosol concentration is substantially the same for each of the focal regions of the three mirrors 54, 56 and 58. Since the scattered radiations cause little attenuation of the incident laser energy, the three mirrors provide better use of the incident laser energy. The concave holographic grating 72 combines the function of a plane ruled grating and two concave mirrors usually associated with a spectrograph. The grating 72 performs the entire function of separating frequencies and properly imaging the entrance slit onto the exit surface of spectrograph 68.

FIG. 2 shows one form of concentrator 24a which includes a hollow housing, preferably cylindrical, including a first section 132 of metal or similar electrically conducting material and a second section 134 of plastic or line insulative material. An inner tube or conduit 136 is generally concentric with the housing and is located within the insulative portion 134. Conduit 136 also is of insulative material, such as plastic, and is provided with a ring 138 of metal or like conducting material at the inlet end which is located ajacent the juncture of housing portions 132, 134. The opposite end of conduit 136 is formed into a right angle elbow which extends out through the wall of housing portion 134 for connection to conduit 38. A source of electrical potential 140 is connected by lines 142 and 144 to housing portion 132 and metal ring 138. Source 140 preferably delivers a pulsating direct voltage which drives off those aerosols which adhere to ring 138. The aerosols are electrostatically forced into a concentrated flow along conduit 136.

FIG. 3 shows another form of concentrator 24b which likewise includes a hollow, preferably cylindrical housing including a conductive portion 150 and an insulative portion 152 and a conduit 154 of insulative material having a portion generally concentric with housing portion 152 and having an inlet end provided with a metal ring 156 adjacent the juncture of housing portions 150, 152. Another conduit 158 of larger diameter surrounds the inlet end portion of conduit in concentric relationship therewith with the axial ends of conduits 154, 158 being coplanar. Both conduits are formed with right angle elbow portions extending through the wall of housing portion 152 at axially spaced locations, and conduit 154 extends through conduit 158 within the housing. A source 160 of direct voltage such as a battery is connected by lines 162 and 164 to housing portion 150 and metal ring 156. Conduit 154 is connected to conduit 38 and the concentrated aerosol stream flows in the direction of arrow 166, with the remaining flow being in the direction of arrow 168. Conduit 158 is connected to a source of clean air which flows in the direction of arrow 170 to prevent depositing of aerosols on metal ring 156. Concentrator 24b operates electrostatically in a manner similar to concentrator 24a to force the aerosols into a concentrated flow along conduit 154. While two forms of concentrator 24 have been described, other forms can be employed.

FIG. 4 shows an arrangement wherein the spectrograph image is detected by a television camera for visual monitoring. A spectrograph 68a receives scattered Raman radiation through entrance slit 70a, and a holographic concave grating 72a converts the Raman radiation to a spectral image in a manner similar to the system of FIG. 1. An intensified television camera 174 is positioned to detect the spectral image. Television camera 174 can be an SEC camera commercially available from Westinghouse Electric Corp. One end of the fiber optics plate 176 is placed on the camera front face, while the other end has a concave surface facing grating 72a in order to reduce optical aberrations of the spectrograph at the exit surface. The output of tube 174 is transmitted to a conventional cathode ray display 180 having a viewing screen 182, and display 180 advantageously can be located remote from the monitoring site. If desired, signals from display 180 can be transmitted by line 184 to conventional telecommunications equipment 186 for further processing and transmission. The Raman scattering signals from many different molecules will be accumulated on the target of the intensified television camera 174 and then are read after a predetermined time by the internal electron gun. The foregoing arrangement can replace many photomultipliers and associated counters. The effective dynamic brightness range of cameral 174 can be increased for use with nominally static one dimensional spectrograph images by selectively controlling the scan repetition rate in accordance with the initially sensed brightness of areas or lines of the object image. In particular, low-intensity portions of the spectrographic output are scanned at low frame rates and high-intensity regions are scanned at the ordinary frame rates of 30 frames per second.

FIG. 5 shows an arrangement for detecting Raman radiation which is an alternative to a spectrograph and which is used in situations where detection of only one chemical specie or pollutant is desired. Raman scattered radiation from a sample cell or chamber 30a leaves optical window 33a and is imaged by a lens 190 to an optical notch filter 192 for rejecting the laser frequency and passing the Raman radiation. Filter 192 can be of the Raman notch filter type commercially available from Omega Optical, Inc. A dichroic mirror 194 of dielectric material is arranged to receive radiation passed by filter 192. Mirror 194 functions to transmit approximately half of the received radiation in a first direction, i.e. horizontally as viewed in FIG. 5, and to reflect the remainder of the radiation in a second direction at an angle to the first direction, i.e. vertically as viewed in FIG. 5. An optical band pass filter 198 is positioned to receive radiation from mirror 194 in one of the directions and to pass Raman radiation of a particular frequency, such as that corresponding to sulphates. The sulphate radiation is focused by a lens 198 to a photomultiplier tube 200 for counting the photons scattered by sulphates in a manner similar to that of the system of FIG. 1. The output of tube 200 is connected by line 202 to digital counters 204 similar to the counters of FIG. 1. A second optical band pass filter 210 is positioned to receive radiation from mirror 194 in the other direction and to pass Raman radiation for nitrogen to provide a calibration signal as in the system of FIG. 1. The nitrogen radiation is focused by a lens 212 to a photomultiplier tube 214 for counting the photons scattered by nitrogen, and the output of tube 214 is connected by a line 216 to counting circuits 204. The counter outputs can be transmitted for arithmetic processing by lines collectively designated 218 in a manner similar to the system of FIG. 1.

From the foregoing description, it is apparent that an improved system and method has been provided for monitoring both ambient gaseous and aerosol pollutants and, in particular, for selectively measuring the concentration of respirable sulphate aerosols of less than about 2 microns particle size in the ambient atmosphere. The concentration is monitored and measured advantageously in a direct manner, without intervention such as filter collection, and it is done on a real-time basis. The optical trap operatively associated with the inspection chamber causing the laser radiation to pass a number of times through the flow of gas or aerosols enhances the signal-to-noise ratio of the system with resultant increase in sulphate concentration measurement sensitivity. The continuous flow of ambient aerosols or gas through the inspection chamber provides the advantages of statistical averaging. The Raman signal from the aerosols is an average of the scattering from a diversity of particle geometries, and the average can be made more accurate by increasing the density of aerosols measured and increasing the measurement time.

As will be apparent to persons skilled in the art, various modifications and adaptations of the system and method above described will become readily apparent without departure from the spirit and scope of the invention, the scope of which is defined in the appended claims.

We claim:

1. A system for monitoring micron size pollutant particles in a gas such as sulphate aerosols in ambient air comprising:
    (a) sampling means for receiving the gas and separating received gas into at least two portions according to the size of the particles in the gas;
    (b) means defining a chamber coupled to said sampling means for receiving one of said particle-containing gas portions, said chamber defining means allowing transmission of light radiation therethrough;
    (c) means coupled to said sampling means and said chamber for moving particles and gas continuously through said sampling means and said chamber during monitoring;
    (d) a laser operatively associated with said chamber for directing a light beam to the particles and gas flowing through said chamber;
    (e) optical means operatively associated with said chamber for causing radiation from said laser to traverse the flow of gas and particles in said chamber a large number of times; and
    (f) radiation responsive means for receiving Raman radiation scattered from the particles and gas flowing through said chamber and providing information as to a characteristic of the particles and gas molecules.

2. The system recited in claim 1 wherein said sampling means comprises a dichotomous sampler for removing the particles having a size greater than about 2 microns.

3. The system recited in claim 1 and means connected between said sampling means and said chamber for concentrating the flow of particles to said chamber into a relatively narrow stream.

4. The system recited in claim 1 wherein said laser is operated in a pulsed mode.

5. The system recited in claim 1 wherein said optical means comprises two concave mirrors operatively associated with said chamber and positioned in opposite facing relation, said mirrors having equal radii of curvature and said mirrors positioned so that said radii are coincident.

6. The system recited in claim 1 wherein said chamber is hollow rectangular in shape having optical windows on at least two surfaces thereof, said laser being positioned to direct light through one of said windows to the central region of said chamber, said optical means comprising two concave mirrors positioned oppositely of said chamber central region, said mirrors being of relative size and location to define an optical trap for the laser radiation in said chamber.

7. The system recited in claim 6 and a concave mirror positioned and oriented in relation to said chamber and the other of said windows for collecting said scattered Raman radiation and a lens positioned and oriented in relation to said other window and in relation to said chamber and radiation responsive means for directing said collected Raman radiation to said radiation responsive means.

8. The system recited in claim 1 and optical means operatively associated with said chamber for collecting said scattered Raman radiation and directing said radiation to said radiation responsive means.

9. The system recited in claim 8 wherein said optical means comprises a concave mirror positioned to collect scattered Raman radiation from said chamber and a lens located between said mirror and said radiation responsive means.

10. The system recited in claim 1 wherein said radiation responsive means comprises:
(a) means separating said Raman radiation into frequency components corresponding to the chemical composition of the particles and gases flowing through said chamber; and
(b) means for converting said frequency components into information providing a measure of the concentration of the particles.

11. The system recited in claim 10 wherein said means separating Raman radiation comprises a spectrograph.

12. The system recited in claim 11 wherein said spectrograph includes an optical grating of the concave holographic type.

13. The system recited in claim 10 wherein said means separating Raman radiation comprises:
(a) an optical notch filter for rejecting radiation at the frequency of said laser;
(b) a dichroic mirror arranged to receive radiation passed by said notch filter, said mirror transmitting approximately half of said radiation in a first direction and reflecting the remainder of said radiation in a second direction at an angle to said first direction;
(c) first and second optical band pass filters positioned to receive radiation in said first and second directions, respectively, each of said filters selected to pass a particular Raman frequency.

14. The system recited in claim 10 wherein said converting means comprises:
(a) photomultiplier means at spaced locations to receive spectrally dispersed radiation images and convert said radiation to electrical pulses corresponding to photons of said Raman radiation; and
(b) counting means coupled to said photomultiplier means to count and accumulate said pulses for providing information of the concentration of particles in the gas flowing through said chamber.

15. The system recited in claim 1 wherein said radiation responsive means comprises a spectrograph having an output image surface on which is found a spectral image of the frequency components of said Raman radiation.

16. The system recited in claim 15 and:
(a) a plurality of photomultiplier elements to receive spectrally dispersed radiation images and convert said radiation to electrical pulses corresponding to photons of said Raman radiation; and
(b) a corresponding plurality of fiber optic elements for optically coupling locations on said spectrograph output image surface to corresponding ones of said photomultiplier elements.

17. The system recited in claim 15 and an intensified television camera tube positioned to receive said spectral image on said output image surface of said spectrograph.

18. The system recited in claim 17 and fiber optic means between said spectrograph output image surface and said television camera tube.

19. A method of monitoring the concentration of micron size particles such as sulphate aerosols in ambient air comprising:
(a) moving ambient air through a separator to remove particles larger than a predetermined size;
(b) moving the air from the separator through a chamber in a substantially continuous flow;
(c) irradiating the air flow in the chamber with light from a laser and optically influencing the radiation from the laser to pass through the air flow a number of times;
(d) collecting Raman radiation scattered from the air flowing through the chamber;
(e) separating the Raman radiation into frequency components corresponding to the chemical composition of the particles in the air flowing through the chamber;
(f) converting the frequency components into electrical pulses representing photons of the Raman radiation; and
(g) counting the electrical pulses to provide a measure of the concentration of the particles in the air flowing through the chamber.

20. The method recited in claim 19 wherein particles greater than about 2 microns in size are removed by the separator.

21. The method recited in claim 19 wherein the laser is selected to avoid excitation of $NO_2$ fluorescence and minimize photomultiplier dark-noise counts.

* * * * *